United States Patent
Jervis (10) Patent No.: US 6,328,729 B1
(45) Date of Patent: Dec. 11, 2001

(54) COLPORRHAPHY METHOD AND APPARATUS

(75) Inventor: James E. Jervis, Atherton, CA (US)

(73) Assignee: General Surgical Innovations, Inc., Norwalk, CT (US)

( * ) Notice: Subject to any disclaimer, the term of this patent is extended or adjusted under 35 U.S.C. 154(b) by 0 days.

(21) Appl. No.: 09/299,886

(22) Filed: Apr. 27, 1999

(51) Int. Cl.⁷ .................................................. A61M 31/00
(52) U.S. Cl. ........................................ 604/515; 604/96.01
(58) Field of Search ................................ 604/96.01, 101, 604/48, 500, 506, 514, 515; 606/108, 167, 170, 180, 184, 185, 191, 192, 193

(56) References Cited

U.S. PATENT DOCUMENTS

| | | | |
|---|---|---|---|
| 2,854,983 | 10/1958 | Baskin | 128/349 |
| 2,936,760 | 5/1960 | Gants | 604/101 |
| 3,039,468 | 6/1962 | Price | 128/347 |
| 3,253,594 | 5/1966 | Mathews et al. | 128/348 |
| 3,417,745 | 12/1968 | Sheldon . | |
| 3,459,175 | 8/1969 | Miller | 128/2 |
| 3,774,596 | 11/1973 | Cook | 128/5 |
| 3,800,788 | 4/1974 | White | 128/83 |
| 3,882,852 | 5/1975 | Sinnreich | 128/4 |
| 3,915,171 | 10/1975 | Shermeta | 604/101 |
| 4,077,412 | 3/1978 | Moossun | 128/347 |
| 4,083,369 | 4/1978 | Sinnreich . | |
| 4,177,814 | 12/1979 | Knepshield et al. | 128/349 |
| 4,198,981 | 4/1980 | Sinnreich | 128/344 |
| 4,312,353 | 1/1982 | Shahbabian | 128/344 |
| 4,326,505 | * 4/1982 | Cropsey | 128/1 |
| 4,501,266 | 2/1985 | McDaniel | 128/69 |
| 4,555,242 | 11/1985 | Saudagar | 604/96 |
| 4,589,868 | 5/1986 | Dretler | 604/96 |
| 4,610,662 | 9/1986 | Weikl et al. | 604/53 |
| 4,651,717 | 3/1987 | Jakubezak | 128/344 |
| 4,706,670 | 11/1987 | Andersen et al. | 128/344 |

(List continued on next page.)

OTHER PUBLICATIONS

Rafael Cinelli, M.D., "The Inflatable Silastic Bag: A Practical Device that Simiplifies Augmentation Mammaplasty." From the Division of Plastic Surgery, Department of Surgery, at the Maimonides Medical Center and Medical Arts Center of New York.

(List continued on next page.)

Primary Examiner—Manuel Mendez (57) ABSTRACT

A balloon apparatus adapted for sequential dissection of an anatomical space and associated methods are provided. The balloon apparatus comprises a tubular member having a lumen, a tunneling member slidably disposed in the lumen of the tubular member, a flattened substantially rectangular balloon sealed about the tubular member, a sleeve which contains the deflated balloon in generally cylindrical rolls about the tunneling member, and a retainer which prevents an inverted substantially heel-shaped portion of the balloon from everting and inflating prior to inflation of the remainder of the balloon. In a preferred method of operation, the balloon apparatus enters an anatomical space whereby the entry point into the anatomical space divides the space into a superior and inferior portions. The tunneling member is advanced into the superior portion of the space and the balloon inflated, thereby dissecting the superior portion of the anatomical space. Then the retainer is released, permitting the heel-shaped portion to be inflated, thereby dissecting the inferior portion of the anatomical space.

19 Claims, 7 Drawing Sheets

U.S. PATENT DOCUMENTS

| | | | |
|---|---|---|---|
| 4,779,611 | 10/1988 | Grooters et al. | 128/4 |
| 4,798,205 | 1/1989 | Bonomo et al. | 128/344 |
| 4,800,901 | 1/1989 | Rosenberg | 128/899 |
| 4,802,479 | 2/1989 | Haber et al. | 128/344 |
| 4,861,334 | 8/1989 | Nawaz | 604/178 |
| 4,875,468 | 10/1989 | Krauter et al. | 128/3 |
| 4,899,729 | 2/1990 | Gill et al. | 128/3 |
| 4,927,412 | 5/1990 | Menasche | 604/96 |
| 4,932,956 | 6/1990 | Reddy et al. | 606/192 |
| 4,966,583 | 10/1990 | Debbas | 604/98 |
| 4,994,047 | 2/1991 | Walker et al. | 604/264 |
| 5,002,557 | 3/1991 | Hasson | 606/191 |
| 5,019,032 * | 5/1991 | Robertson | 600/29 |
| 5,042,976 | 8/1991 | Ishitsu et al. | 604/96 |
| 5,043,336 | 8/1991 | Kieturakis et al. | 606/167 |
| 5,122,122 | 6/1992 | Allgood | 604/178 |
| 5,163,949 | 11/1992 | Bonutti | 606/192 |
| 5,197,971 | 3/1993 | Bonutti | 606/192 |
| 5,295,994 | 3/1994 | Bonutti | 604/102 |
| 5,320,611 | 6/1994 | Bonutti et al. | 604/264 |
| 5,331,975 | 7/1994 | Bonutti | 128/898 |
| 5,345,927 | 9/1994 | Bonutti | 128/20 |
| 5,370,134 * | 12/1994 | Chin et al. | 604/104 |
| 5,439,455 | 8/1995 | Kieturakis et al. | 604/264 |
| 5,454,365 | 10/1995 | Bonutti | 600/204 |
| 5,464,403 | 11/1995 | Kieturakis et al. | 606/1 |
| 5,496,345 | 3/1996 | Kieturakis et al. | 606/192 |
| 5,514,091 | 5/1996 | Yoon | 604/101 |
| 5,514,153 | 5/1996 | Bonutti | 606/190 |
| 5,540,711 | 7/1996 | Kieturakis et al. | 606/192 |
| 5,601,590 | 2/1997 | Bonutti et al. | 606/192 |
| 5,607,443 | 3/1997 | Kieturakis et al. | 606/192 |
| 5,667,520 | 9/1997 | Bonutti | 606/190 |
| 5,685,826 | 11/1997 | Bonutti | 606/204 |
| 5,702,416 | 12/1997 | Kieturakis et al. | 606/193 |
| 5,707,390 | 1/1998 | Bonutti | 606/204 |
| 5,716,325 | 2/1998 | Bonutti | 300/204 |
| 5,730,756 | 3/1998 | Kieturakis et al. | 606/190 |
| 5,772,680 | 6/1998 | Kieturakis et al. | 606/190 |
| 5,817,123 | 10/1998 | Kieturakis et al. | 606/192 |
| 5,827,318 | 10/1998 | Bonutti | 606/190 |
| 5,836,961 | 11/1998 | Kieturakis et al. | 606/190 |
| 5,860,997 | 1/1999 | Bonutti | 606/190 |
| 5,888,196 | 3/1999 | Bonutti | 600/204 |
| 5,954,739 | 9/1999 | Bonutti | 606/190 |
| 6,004,337 | 12/1999 | Kieturakis et al. | 606/190 |
| 6,017,305 | 1/2000 | Bonutti | 600/207 |
| 6,042,596 | 3/2000 | Bonutti | 606/190 |
| 6,102,928 | 8/2000 | Bonutti | 606/190 |

OTHER PUBLICATIONS

Bruce M. Rigg, M.D., "Inflatable Device for Intraoperative Use During Augmentation Mammaplasty." Reconstructive Surgery, May 1982.

Gordon H. Sasaki, M.D., "Intraoperative Sustained Limited Expansion (ISLE) as an Immediate Reconstructive Technique." Clinics in Plastic Surgery –vol. 14, No. 3, July 1987.

Gordon H. Sasaki, M.D., "Intraoperative Expansion" as an Immediate Reconstructive Technique. Facial Plastic Surgery, 5:4, July 1988.

Dr. Sanchez de Badajoz Chammorro et al., "Endoscopic Cervical Anchorage, New Treatment for Stress Incontinence," Archivos Españoles de Urologia: vol. 41, Issue 2, pp. 127–130, 1988.

Dr. Sanchez de Badajoz Chammorro et al., "Stress Incontinence: A New Endoscopic Approach," vol. 36, No. 5, pp. 403–405, November 1990.

Eduardo Sanchez de Badajoz et al., Uretropexia Laparoscopica, Arch. Esp. de Urol. 46,7 (642–644), 1993. English Translation Attached.

Henry T. Hoffman, M.D., and Shan H. Baker, M.D., "Nasal Reconstruction with the Rapidly Expanded Forehead Flay," Larynogoscope, 99:1096–1098, 1989.

R. Wittmoser, "Retroperitoneoscopy: A Preliminary Report", pp. 760–761, 1976.

Sanchez, et al., "Extraperitoneal Laparoscopic Urethropexy," Arch. Esp. de Urol., 47, 4(415–418), 1994.

* cited by examiner fig.1 fig.2 fig. 8 fig.9

FIG. 10

COLPORRHAPHY METHOD AND APPARATUS

FIELD OF THE INVENTION

This invention relates to surgical methods. More particularly, this invention relates to a colporrhaphy method using balloon dissection.

BACKGROUND OF THE INVENTION

As a result of overdistention during childbirth, infection or other trauma, damage to the female pelvic anatomy may occur, manifesting in vaginal prolapse, or in less severe instance, in either cystocele or rectocele, or their combination. Cystocele results when the bladder herniates into the anterior vaginal wall. Similarly, rectocele results when the rectum herniates into the posterior vaginal wall.

The vagina lies between the rectum and the bladder. Normally, there are planes of cleavage or potential spaces occurring between the vagina and these structures whereby the vagina, the rectum and the bladder may function and move independently of one another. The potential space between the bladder and the vagina is denoted the vesicovaginal space whereas the potential space between the vagina and the rectum is denoted the rectovaginal space. These "spaces" are generally filled with adipose tissue, providing little connectivity so that the structures are relatively independent of one another.

Both cystocele and rectocele are often accompanied by "loss" of the vesicovaginal space or the rectovaginal space, or their combination. Such "loss" is manifested in an increase of adhesions between the adjacent anatomical structures, often holding them in an unnatural anatomical position. For example, a symptom of cystocele is an unnatural protrusion or bulge of the anterior vaginal wall that is aggravated by gravity and accompanied by urinary incontinence. Because of these adhesions within these spaces, impaired or potential mobility of one related structure necessarily involves the adjacent structure, and independent function is compromised. Therefore, any surgical repair tending to return the pelvic anatomy to normalcy advantageously includes restoration of independent mobility of these fused structures. This can usually be accomplished, at least in part, by dissection of the adhesions within these pelvic spaces.

Release of these adhesions through conventional colporrhaphy entails extensive incisions within the vagina, followed by manual dissection to the anatomic limits of the spaces. (see, e.g., Mastery of Surgery, $2^{nd}$ Ed., Vol. II, pp. 1532–1549). This approach is tedious, requires cautery to control bleeding, and causes extensive trauma to tissue adjacent to the spaces, which may result in additional subsequent adhesions. Thus there is a need in the art for improved methods of dissecting the vesicovaginal and rectovaginal spaces which reduce trauma to the patient and are less time consuming.

Compared to manual dissection, a less traumatic form of dissection is that accomplished by inflation of a balloon. Balloon dissection is blunt by nature, and tends to minimize bleeding, particularly if the balloon is left in place briefly after inflation as a tamponade. Additionally, the balloon will tend naturally to find the extremes of the anatomic space. Thus, balloon dissection of the vesicovaginal space (VVS) and rectovaginal space (RVS) will provide a less traumatic form of dissection. In, e.g., U.S. Pat. Nos. 5,496,345, 5,814,060, and 5,514,153, a variety of balloon dissection apparatus and methods of surgical procedures using such apparatus are disclosed, which disclosures are hereby incorporated by reference. Despite the advances disclosed by these references, a need exists for a balloon dissection apparatus adapted for dissecting the VVS and RVS, particularly wherein the balloon dissection apparatus enters these spaces through an incision within the vagina.

SUMMARY OF THE INVENTION

In one innovative aspect of the invention, a balloon apparatus adapted for dissection of the VVS and the RVS is provided. The balloon apparatus comprises a tubular member connected to a proximal housing having a stop wherein a lumen extends through the proximal housing and tubular member. A flattened substantially rectangular balloon constructed from a non-elastomeric material seals about the tubular member. A tunneling member attached to a proximal handle having a stop is slidably disposed within the lumen of the tubular member and proximal housing wherein a seat on the proximal housing may engage the stop located on the proximal handle. The tunneling member may be hollow to accommodate a laparoscope inserted in a port located on the proximal handle. When deflated, the balloon is disposed in a generally cylindrical roll or gathered about the tunneling member. A longitudinally extending sleeve surrounds the deflated balloon to retain the balloon in the generally cylindrical roll about the tunneling member. A weakened region of the sleeve permits the sleeve to separate from the deflated balloon. The weakened region may comprise a series of longitudinally extending co-linear perforations of the sleeve. A balloon inflation tube in fluid communication with the interior of the balloon is provided for connection to an inflation source. When the stop of the handle and the seat of the proximal housing are engaged and the sleeve surrounds the deflated balloon, the distal end of the tunneling member is adjacent the distal end of balloon wherein the tunneling member, the balloon, and the sleeve form a blunt-tipped tunneling assembly.

In a preferred embodiment, the balloon comprises a distal portion and a substantially heel-shaped portion extending proximally at an oblique angle from the distal end of the tubular member. The heel-shaped portion is inverted into the balloon when the balloon is deflated. A retainer prevents the heel-shaped portion from everting. The retainer may comprise a number of alternate embodiments. In one embodiment, the retainer comprises a modification of the longitudinal perforations wherein the perforations comprise a proximal portion and a distal portion. The proximal portion of the longitudinal perforations, which is located adjacent the heel-shaped portion of the balloon, contains perforations spaced apart a first predetermined distance. The perforations of the distal portion are spaced apart a second predetermined distance, wherein the first predetermined distance is greater than the second predetermined distance, thereby inhibiting separation of the perforations in the proximal portion relative to the distal portion. In another embodiment, the retainer may comprise a ring-shaped member disposed about the tunneling member. The distal end of the inverted heel-shaped portion is attached to the ring-shaped member. Displacing the tunneling member proximal to the ring-shaped member releases the heel-shaped portion of the balloon. In yet another embodiment, the retainer may comprise an external ring-shaped member disposed about the sleeve surrounding the deflated balloon. The external ring-shaped member overlaps the inverted heel-shaped portion of the balloon. A connector attached to the external ring-shaped member allows a clinician to proximally withdraw the external ring-shaped member, releasing the inverted heel-shaped portion of the balloon. In yet another embodiment, no retainer is necessary; the frictional resistance of the inverted portion to becoming everted acts as a "retainer" for the inverted heel-shaped portion.

In another innovative aspect of the invention, methods of dissecting an anatomical space (either the RVS and VVS) using the balloon apparatus are provided. The clinician makes an incision to provide access to the anatomical space. With the sleeve maintaining the deflated balloon in a generally cylindrical roll about the tunneling member, and with the stop and seat engaged so that the distal end of the tunneling member is adjacent the distal end of balloon wherein the distal ends of the tunneling member, the balloon, and the sleeve form a blunt-tipped tunneling assembly, the clinician inserts the tunneling assembly into the incision in the anatomical space. The clinician then advances the tunneling member for a sufficient distance into the space such that the balloon may access the space, whereupon the balloon is inflated. As the balloon inflates, it exerts pressure on the weakened region of the sleeve to cause the weakened region to separate, releasing the balloon from the sleeve. The balloon may then expand to cause dissection within the space.

In a preferred method, the clinician accesses an anatomical space through an incision such that the insertion point divides the space into a superior portion and an inferior portion. The balloon apparatus includes the distal portion, the inverted heel-shaped portion and the retainer described previously. After inserting the tunneling assembly into the incision, the clinician advances the tunneling assembly within the superior portion of the space so that the distal end of the tunneling assembly is adjacent the superior end of the space. The balloon is then inflated to separate the weakened region of the sleeve, allowing the distal portion of the balloon to expand and dissect the superior portion of the space. The clinician then releases the retainer to allow the heel-shaped portion of the balloon to inflate and dissect the inferior portion of the space.

DETAILED DESCRIPTION OF THE INVENTION

Figure 1:
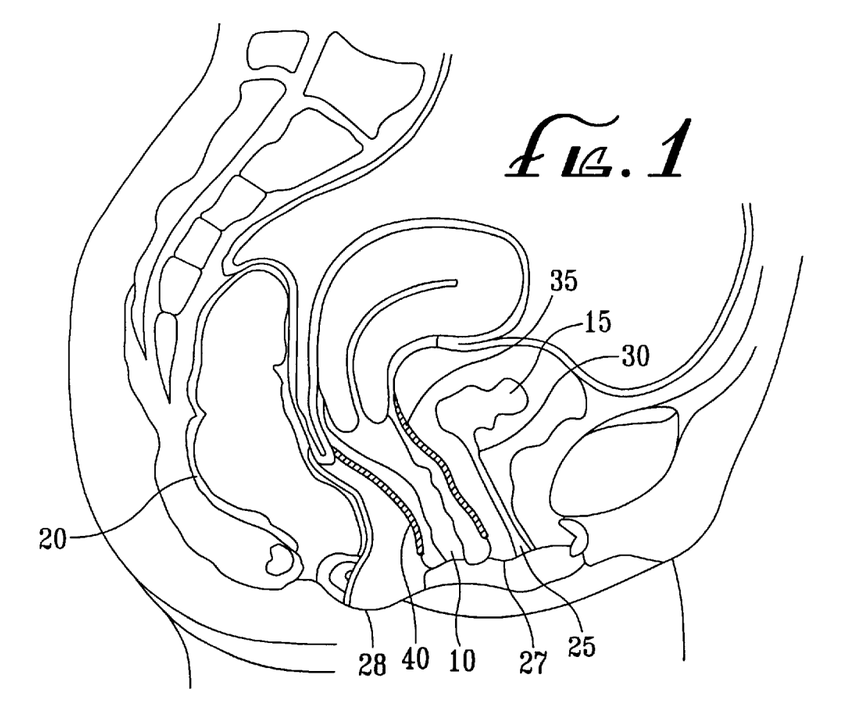
FIG. 1 is a mid-sagital section showing the vagina and surrounding spaces and structures.
Figure 2:
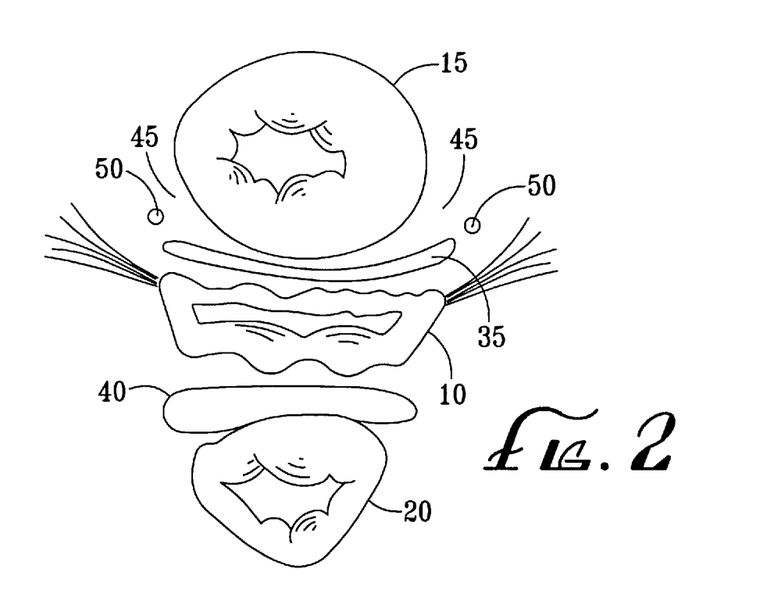
FIG. 2 is a transverse section showing the vagina and surrounding spaces and structures.

Turning now to FIGS. 1 and 2, the female pelvic anatomy is illustrated. The vagina 10 lies between the bladder 15 and the rectum 20. Extending from the bladder 15 is the urethra 25 that joins the bladder 15 at the urethrovesical junction 30 (or bladder neck). Between the bladder 15 and the vagina 10 is the vesicovaginal space (VVS) 35. Similarly, between the rectum 20 and the vagina 10 is the rectovaginal space (RVS) 40. The VVS 35 extends laterally into the bladder pillars 45 within which are found the ureters 50.

The present invention comprises balloon apparatus adapted for methods of colporrhaphy in which the VVS 35 and the RVS 40 are dissected through balloon dissection. Referring now to FIGS. 3–7, the balloon apparatus 75 includes a tubular member 80 attached to a proximal housing 85. A lumen extends through the tubular member 80 and proximal housing 85 to slidably accommodate a tunneling member 90 attached to a proximal handle 95 adapted to be grasped by the human hand. The tunneling member 90 may be straight, curved or malleable for adjustment into an appropriate shape by a clinician. Moreover, the tunneling member 90 may be rigid or sufficiently flexible so that the tunneling member 90 bends to follow the anatomical space as it is being inserted while still providing enough rigidity to make possible a blunt dissection with tunneling member 90 to facilitate the introduction of the balloon to a desired location within the anatomical spaces. In addition, the tunneling member 90 may have a bore extending therethrough to accommodate an endoscope (not illustrated) or may be solid.

Because the proximal housing 85 has surface adapted to act as a seat 100 which engages a similar surface acting as a stop 105 on the proximal handle 95, the tunneling member 90 may only be distally displaced a certain distance within the lumen of the proximal housing 85 and tubular member 80 before the seat 100 and stop 105 engage, preventing further distal displacement of tunneling member 90. This prevents the tunneling member 90 from perforating the flattened substantially rectangular balloon 110 sealed about and attached to the tubular member 80. Because the balloon 110 seals about the tubular member 80, the tunneling member 90 is disposed within the interior of the balloon 1 10. The balloon 110 and the tunneling member 90 are preferably both constructed from an optically clear material to facilitate imaging through a laparoscope inserted within the lumen of the tunneling member 90. The tunneling member 90 may have a rounded, substantially hemispherical tip or may have an open, yet blunt, distal extremity to permit observation through a laparoscope through the open distal end.

The balloon 110 when deflated has a flattened substantially rectangular shape adapted for dissection of either the RVS or the WS. The balloon 110 is preferably formed of a non-elastomeric, medical-grade material of a suitable type such as polyurethane. Thus, the balloon 110 can be formed of two sheets of this material that have their outer margins bonded together by suitable means such as by a heat seal extending around the perimeter of the flattened balloon 110. The balloon is secured to the tubular member 80 in a suitable airtight fashion such as by an adhesive. Because the tunneling member 90 is disposed within the interior of the balloon 110, it is preferably mounted within a disk-type pneumatic seal 115 in alignment with the lumen of the tubular member 80 and the proximal housing 85. The pneumatic seal 115 may be located in either the tubular member 80 or the proximal housing 85. A balloon inflation tube 122 in fluid communication with the interior of the balloon 110 is provided for connection to an inflation source. As a suitable fluid such as saline is used to inflate the balloon 110 by forcing the fluid through the balloon inflation tube 122, the pneumatic seal 115 prevents the fluid from leaking between the tunneling member 90 and the tubular member 80 (and similarly between the tunneling member 90 and the proximal housing 85. If the tunneling member 90 is open at its distal end, an additional pneumatic seal (not illustrated) in alignment with the lumen of the tunneling member 90 would seal about an inserted laparoscope, preventing fluid from leaking out of the balloon 110 through the lumen of the tunneling member 90.

Figure 3:
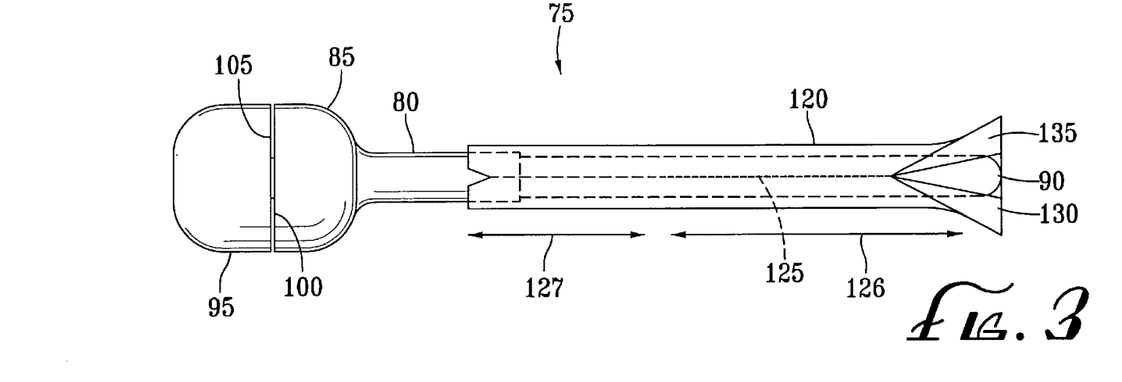
FIG. 3 is a plan view of the balloon apparatus, partially cut-away, according to one embodiment of the present invention.
Figures 5, 6:
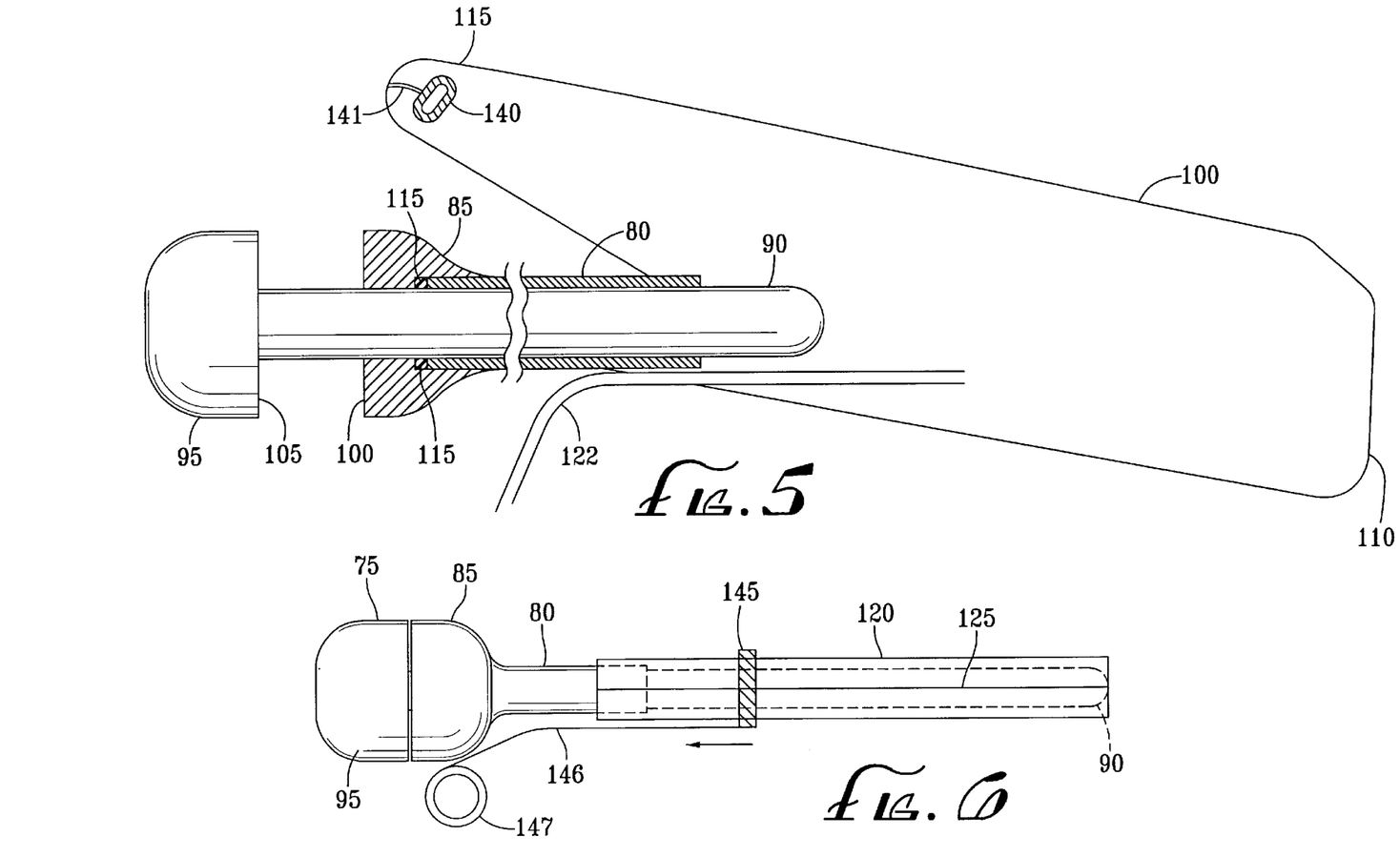
FIG. 5 is a plan view, partially cut-away of the balloon apparatus adapted for insertion through an incision within the vagina with the heel portion everted according to one embodiment of the present invention.
FIG. 6 is a plan view, partially cut-away of the balloon apparatus adapted for insertion through an incision within the vagina according to one embodiment of the present invention.

A sleeve 120 extends longitudinally along the balloon 110 and is formed of the same or similar material as the balloon 110. The sleeve 120 may be formed integral with the balloon 110 or separate therefrom and adhered thereto by suitable means such as an adhesive. The sleeve 120 has a weakened region (shown as longitudinally spaced apart perforations 125 in FIG. 3) which permits the sleeve to separate along the weakened region into at least two parts 130 and 135. Alternatively, the weakened region could consist of an easily torn seam or other releasable means. When deflated, the side margins of the balloon 110 can be rolled inwardly or gathered toward the tunneling member 90 to permit the balloon to be folded into a generally cylindrical configuration as shown in FIGS. 3 and 6. The sleeve 120 then retains the folded balloon 110 about the tunneling member 90 so that the combination of the sleeve 120, the balloon 110 and the tunneling member 90 form a blunt-tipped tunneling assembly. As the balloon is inflated, the perforations 125 in the sleeve 120 begin to separate, a process shown beginning, for example, at the distal tip of the tunneling member 90 in FIG. 3.

Figure 4:
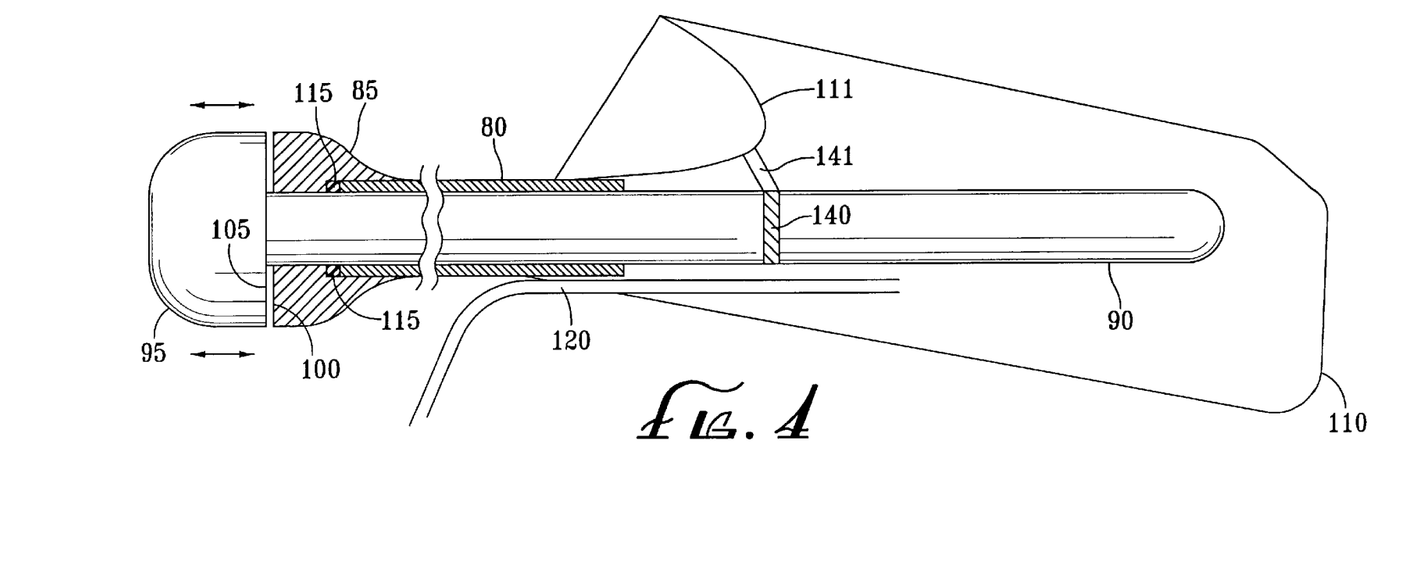
FIG. 4 is a plan view, partially cut-away of the balloon apparatus adapted for insertion through an incision within the vagina prior to the balloon being gathered around the tunneling member according to one embodiment of the present invention.
Figure 7:
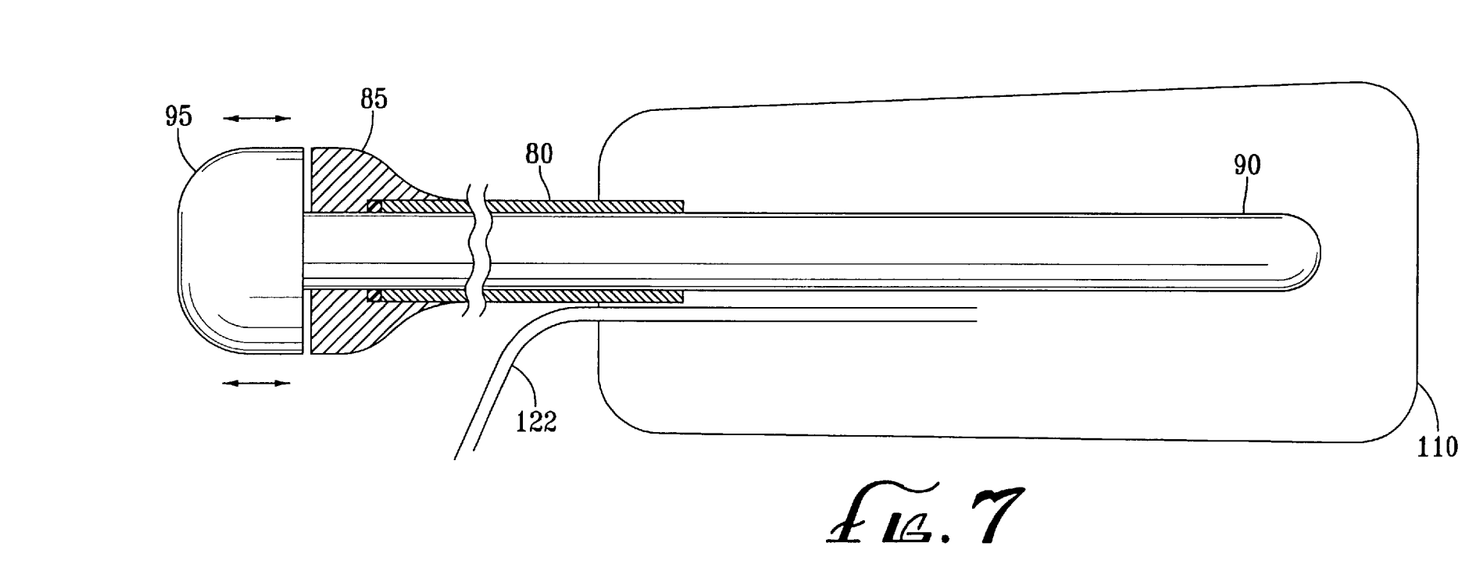
FIG. 7 is a plan view, partially cut-away of the balloon apparatus adapted for insertion through an incision within the perineum according to one embodiment of the present invention.
Figure 8:
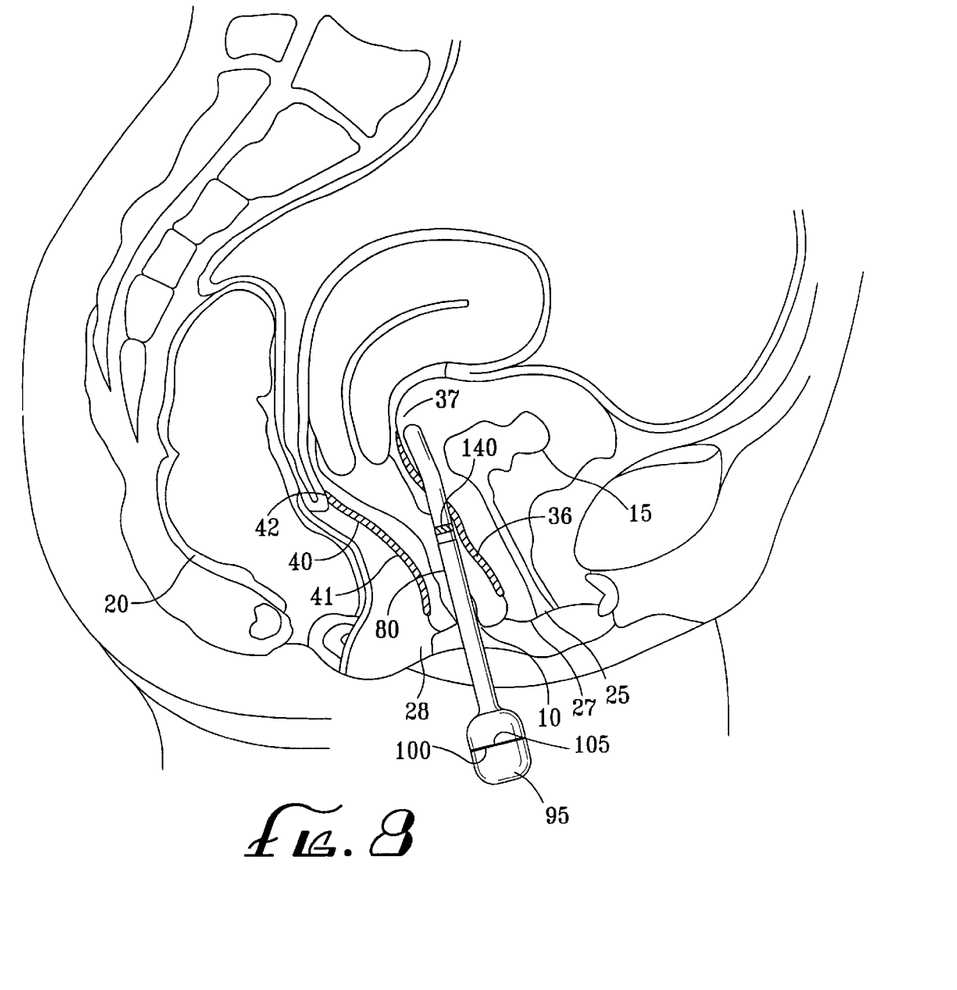
FIG. 8 is a mid-sagital section of the vagina and its surrounding spaces and structures, wherein the tunneling member of the balloon apparatus is being advanced to the superior end of the VVS.

The balloon 110 may be orientated differently with respect to the tunneling member 90 and the tubular member 80 depending upon the insertion point within the patient. Should the VVS 35 be entered through an incision outside the anterior wall 27 of the vagina 10 (location 27) or should the RVS 40 be entered through an incision in the perineum 28, the longitudinal axis of the balloon will be substantially parallel to the longitudinal axis of the tunneling member as illustrated in FIG. 7. Instead, if either the VVS 35 or the RVS 40 are entered through an incision within the vagina 10, the longitudinal axis of the balloon 110 is orientated obliquely to the longitudinal axis of the tunneling member 90 as illustrated in FIGS. 4 and 5. The difference in orientation may be seen with respect to FIG. 8, illustrating insertion of the balloon apparatus 75 into the VVS 35 through an intravaginal incision. As compared with entering the VVS 35 through an incision adjacent the anterior wall of the vagina (denoted as location 27), an intravaginal incision allows a less traumatic and more direct access to the VVS 35. However, the balloon apparatus 75 enters the VVS 35 at an oblique angle when inserted through an intravaginal incision, thus requiring the oblique orientation of the balloon 110 with respect to the tunneling member 90. If, instead, the balloon apparatus 75 enters the VVS 35 through an incision at location 27, external to the vagina 10, the longitudinal axis of the tunneling member 90 will be substantially parallel to the "longitudinal axis" of the VVS 35. Thus, for incisions at location 27, the balloon 110 should be orientated as illustrated with respect to the tunneling member 90 as illustrated in FIG. 7 whereas for intravaginal access, the balloon 110 should be obliquely orientated with respect to the tunneling member 90. Note that while FIG. 8 illustrates dissection of the VVS 35, the discussed balloon 110 orientation with respect to the tunneling member 90 is equally applicable to dissection of the RVS 40.

Figure 9:
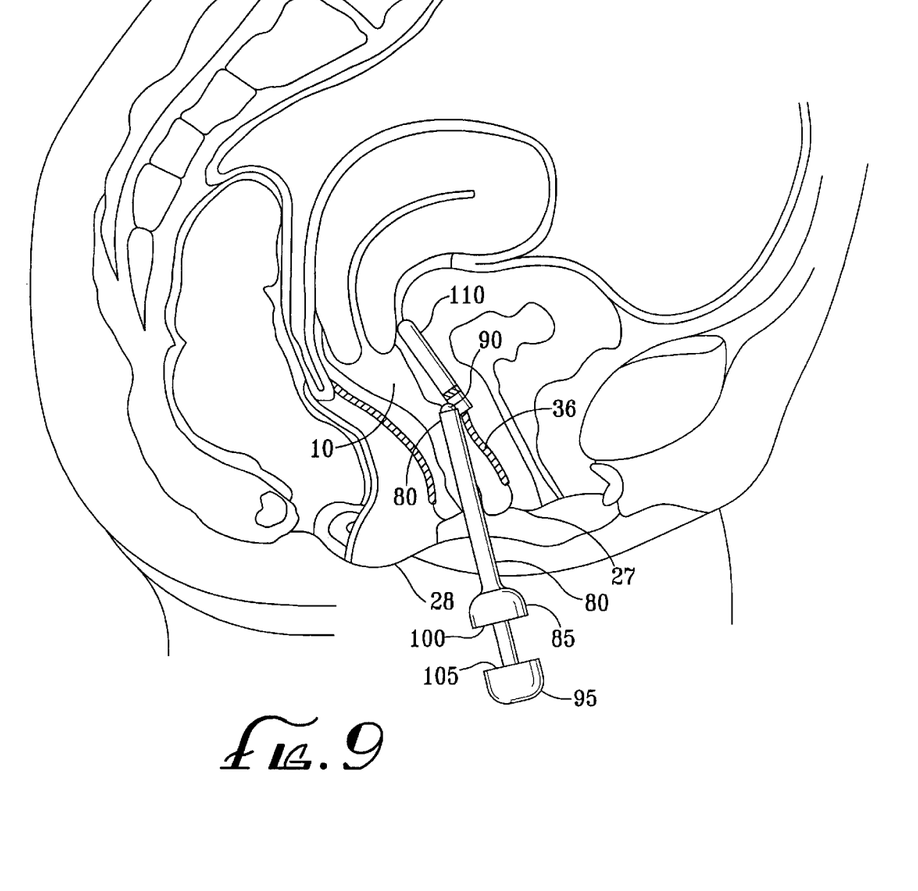
FIG. 9 is a mid-sagital section of the vagina and its surrounding spaces and structures, wherein the portion of the balloon distal to the inverted proximal heel-shaped portion is inflated and dissects the superior portion of the VVS.
Figure 10:
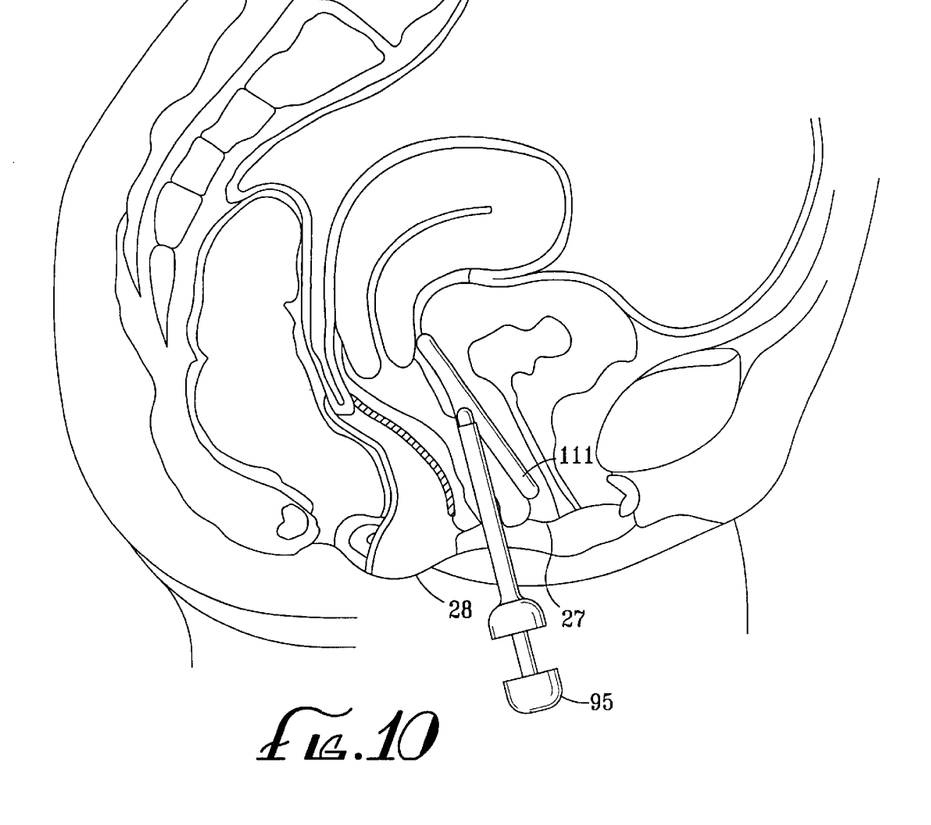
FIG. 10 is a mid-sagital section of the vagina and its surrounding spaces and structures, wherein the proximal heel-shaped portion is inflated and dissects the inferior portion of the VVS.

Because it is preferable to access the RVS 40 and the VVS 35 through an intravaginal incision, the tunneling member 90 (and hence the balloon 110) will enter the space such that the space is divided into a superior portion and an inferior portion as defined with respect to the insertion point, as illustrated in FIG. 8. Note that FIGS. 8 through 10 illustrate dissection of the VVS 35 but the method illustrated is equally applicable to dissection of the RVS 40. The tunneling member cannot dissect the inferior portion 36 of the VVS 35. Thus, as will be hereinafter described, a sequential balloon inflation method may be preferable when intravaginal entry is used. Instead, if the balloon apparatus 75 enters through the perineum 28 (for the RVS 40) or at location 27 (for the VVS 35), the tunneling member 90 will directly access the inferior portion of the space. Because the balloon 110 is disposed about the tunneling member 90, it too can directly access the entire space in such instances, and the entire balloon 110 may inflate as a unit rather than sequentially. Thus, for such an embodiment, the balloon needs no retainer to enable a sequential inflation. Moreover, such an embodiment may not require any portion of the balloon to be inverted.

When the balloon 110 is orientated obliquely with respect to the longitudinal axis of the tunneling member 90, the balloon 110 includes a generally heel-shaped portion 111 extending proximally from the distal end of the tubular member 80 and a distal portion. It is this heel-shaped portion 111 which is used to dissect the inferior portions 36 and 41 of the VVS 35 and the RVS 40, respectively. Prior to inflation of the balloon 110, the heel-shaped portion is inverted into the interior of the balloon 110 as illustrated in FIG. 4. A retainer delays inflation of this inverted heel-shaped portion 111 so that the heel-shaped portion 111 may inflate subsequent to the inflation of the distal portion of the balloon 110. A number of alternative embodiments for the retainer are provided. For example, in one embodiment, the retainer consists of the frictional resistance provided by inverting the heel-shaped portion 111. Because the remainder of the balloon 110 is not inverted, the heel-shaped portion 111 will inflate only after the distal portion of the balloon 110 has inflated because of this frictional resistance. In another embodiment, the longitudinal perforations 125 comprise a proximal and a distal portion. The proximal portion 127 has perforations spaced apart by a first predetermined distance and is located adjacent the inverted heel-shaped portion 111. The distal portion 126, which comprises the remainder of the longitudinal perforations 125, contains perforations spaced apart a second predetermined distance. Because the second predetermined distance is less than the first predetermined distance, the distal portion 126 will separate more readily than the proximal portion 127. Thus, as fluid is pumped through the balloon inflation tube 122, the balloon will preferentially inflate in the region adjacent to the distal portion 126. Subsequently, as the pressure within the balloon 110 increases, the proximal portion 127 of the sleeve 120 will separate, allowing the heel-shaped portion 111 to inflate.

Alternatively, the clinician may desire a manually controllable retainer. FIG. 4 illustrates one such embodiment. The retainer comprises a ring-shaped member 140 disposed about the tunneling member 90. The inverted heel-shaped portion 111 connects to the ring-shaped member 140 by a cord 141 or similar means. Because the inverted heel-shaped portion 111 connects to the ring-shaped member 140, it cannot evert (and hence cannot inflate) so long as the ring-shaped member 140 is disposed about the tunneling member 90. However, if a clinician displaces the tunneling member 90 with respect to the balloon 110 such that its distal end is proximal to the ring-shaped member 140 as illustrated in FIG. 5, the ring-shaped member 140 is released, allowing the heel-shaped portion to evert and inflate.

An alternate embodiment of a manually controllable retainer is illustrated in FIG. 6. The retainer comprises an external ring-shaped member 145 disposed about the sleeve 120 in a location adjacent the inverted heel-shaped portion 111. The sleeve 120 contains the deflated balloon 110 in a generally cylindrical roll about the tunneling member 90 as described previously. As the balloon 110 is inflated, it separates the sleeve 120 along the perforations 125. However, the perforations 125 cannot separate in the vicinity of the external ring-shaped member 145. Thus, the balloon cannot inflate at this location, preventing the inverted heel-shaped portion 111 from inflating. A connecting means such as the cord 146 connects the external-ring shaped member 145 to a handle 147. A clinician releases the inverted heel-shaped member 111 by pulling on the handle 147 to displace the external ring-shaped member 147 proximal to the balloon 110. The perforations 125 which had been prevented from separating by the external ring-shaped member may now separate, permitting the heel-shaped portion 111 to evert and inflate. Note that because the external ring-shaped member 145 is outside the sleeve 120, it will experience frictional forces from the body as the tunneling member 90 is inserted into an incision. Such forces would proximally displace the external ring-shaped member, perhaps permitting a premature inflation of the heel-shaped portion 111. Thus, in such embodiments, the external ring-shaped member should have a releasable connection (not illustrated) to the sleeve 120. This releasable connection (such as a small portion of adhesive) would resist proximal displacement from frictional forces exerted during insertion of the tunneling member 90 into the body, but would still allow a clinician to break the releasable connection by a proximal tug on the handle 147. Those of ordinary skill in the art will appreciate that many other embodiments of a retainer may be implemented.

The present invention also includes methods of dissecting the RVS 40 and the VVS 35 by using the balloon apparatus 75. To access the anatomical spaces, the clinician must make an incision, either intravaginally, in the perineum 28, or externally to the anterior wall of the vagina (location 27). With the deflated balloon 110 retained in a generally cylindrical roll about the tunneling member 90 by the sleeve 120 such that the combination of the balloon 110, the sleeve 120, and the tunneling member 90 form a blunt-tipped tunneling assembly, the clinician advances the tunneling member 90 through the incision into the anatomical space. Because the tunneling member 90 is preferably semi-rigid, as the tunneling member 90 advances through the anatomical space it bends to follow any deviations from linearity within the space while providing enough rigidity to permit such blunt dissection. Such bending of the tunneling member 90 is illustrated in FIG. 8. The clinician continues to advance the tunneling member 90 until the distal end of the tunneling member reaches the superior extent of the anatomical space. Turning now to FIG. 9, the clinician may then pump fluid (using a syringe or other pumping means) through the balloon inflation tube to begin inflating the balloon 110. Because FIGS. 8 through 10 illustrate a dissection of the VVS 35 through an intravaginal incision, the balloon must have a retainer to prevent inflation of the inverted heel-shaped portion 111 of the balloon 110 while the superior portion of the VVS 35 is dissected. FIGS. 8 through 10 illustrate a retainer comprising the ring-shaped member 141 disposed about the tunneling member 90 as described previously. Thus, until the clinician is ready to dissect the inferior portion 36 of the VVS 35, the tunneling member continues to retain the ring-shaped member 141. As the clinician pumps fluid into the balloon 110, the longitudinal perforations 125 separate, allowing the distal portion of the balloon to begin inflating. The balloon 110 progressively unwraps with its side margins rolling outwardly from the center while expanding or extending to cause progressive separation or dissection of tissue along its weakest points by application of forces generally perpendicular to the tissue planes to open the superior portion of the VVS 35.

The clinician can monitor the dissection of the VVS 35 through a laparoscope inserted in the port on the proximal handle 95 into the lumen of the tunneling member 90. In addition, the location of the tunneling member 90 and the formation of the anatomical spaces may be monitored with ultrasound or x-ray imaging means. After the desired dissection of the superior portion 37 of the VVS 35 has been performed, the clinician may dissect the inferior portion 36 of the VVS 35. Note that because the heel-shaped portion 111 extends proximally (when inflated) beyond the distal end of the tubular member 80, the balloon apparatus 75 must be inserted such that at least the distal end of the tubular member accesses or enters the VVS 35. This assures that the heel-shaped portion 111 will expand within the inferior portion 36 of the VVS 35. To begin dissection of the inferior portion 36, the clinician must release the ring-shaped member 140 from the tunneling member 90. The clinician does so by retracting the proximal handle 95 from the proximal housing 85 such that the distal end of the tunneling member 90 is proximal to the ring-shaped member 140. The ring-shaped member 140 is then free from tunneling member 90, allowing fluid to evert and inflate the heel-shaped portion 111. As illustrated in FIG. 10, the heel-shaped portion 111 dissects the inferior portion 36 of the VVS 35 as it inflates.

Should the VVS be accessed through an incision external to the anterior vaginal wall 27, the clinician no longer needs to employ a sequential dissection method as illustrated in FIGS. 8 through 10 because the tunneling member 90 (and hence the balloon 110) occupies the entire longitudinal extent of the VVS from its most inferior extent to the most superior extent of the space. Thus, the balloon may be inflated in one step, dissecting the entire space, when such an incision is employed using the balloon embodiment of FIG. 7. However, such an external access to VVS is less direct than an access through an intravaginal incision.

Note that dissection of the RVS 40 through an intravaginal incision will follow an analogous sequential deployment using the embodiment of the balloon 110 with the inverted heel portion 111. Similarly, if the RVS is accessed through an external incision in the perineum 28, the balloon may be inflated in one step, dissecting the entire space, using the balloon embodiment of FIG. 7.

From the foregoing, it can be seen that the apparatus and method or procedures of the present invention can be utilized in various laparoscopic procedures besides dissection of the RVS and the VVS. For example, the balloon embodiments and methods used to perform dissection through an intravaginal incision are easily adapted to dissection of other anatomic spaces requiring such bi-directional or sequential deployment. Those of ordinary skill in the art will perceive this and other improvements, changes and modifications of the present invention. Such improvements, changes and modifications within the skill of the art are intended to be covered by the appended claims.

What is claimed is:

1. A method of dissecting an anatomic space adjacent a vagina, comprising the steps of:
   providing a balloon apparatus for sequential dissection of the anatomic space adjacent the vagina, said apparatus comprising:
   a tubular member having a lumen;
   a proximal housing attached to the proximal end of said tubular member, said proximal housing having a seat, said proximal housing having a lumen in alignment with said lumen of said tubular member;
   a tunneling member having a blunt distal end, said tunneling member slidably disposed in said lumen of said tubular member and said lumen of said proximal housing;

a proximal handle attached to the proximal end of said tunneling member, said proximal handle having a stop formed to engage said seat of said proximal housing;

a flattened substantially rectangular balloon, said balloon being deflated and formed into a roll surrounding said tunneling member during tunneling through tissue, said balloon sealed about said tubular member, said balloon comprising a distal portion and a substantially heel-shaped portion, said heel-shaped portion extending proximally beyond the distal end of said tubular member, said heel-shaped portion inverted into said balloon before said balloon is formed into the roll surrounding said tunneling member;

a sleeve surrounding at least a portion of said deflated balloon and said tunneling member wherein said sleeve, said balloon and said tunneling member form a blunt-tipped tunneling assembly, said sleeve being provided with a weakened region to permit said sleeve to separate from said deflated balloon thereby allowing said balloon to inflate; and a retainer which prevents said heel-shaped portion from inflating, said retainer being releasable such that said heel-shaped portion inflates subsequently after said distal portion of said balloon inflates;

making an incision within the vagina to provide access to the anatomical space adjacent the vagina;

inserting said blunt-tipped tunneling assembly into said anatomical space, said insertion point in said anatomical space dividing said anatomical space into an inferior portion and a superior portion;

advancing said tunneling member into said superior portion of said anatomical space;

pumping fluid into said balloon to separate said sleeve in said weakened region, said distal portion of said balloon thereby inflating and dissecting said superior portion of said anatomical space, said inverted heel-shaped portion of the balloon being retained by said retainer; and releasing said retainer wherein said heel-shaped portion may evert and inflate, said heel-shaped portion thereby dissecting said inferior portion of said anatomical space.

2. The method of claim 1 wherein said anatomical space is the vesicovaginal space.

3. The method of claim 1 wherein said anatomical space is the rectovaginal space.

4. A colporrhaphy method comprising the steps of:

making an incision to provide access to an anatomical space adjacent to a vagina;

introducing a deflated balloon into the incision and directing it to a location between inferior and superior portions of said anatomical space; and inflating the balloon for the purpose of dissecting the superior portion of the anatomical space, and then dissecting the inferior portion of the anatomical space.

5. The method of claim 4 wherein said anatomical space is the vesicovaginal space.

6. The method of claim 4 wherein said anatomical space is the rectovaginal space.

7. The method of claim 4 wherein said incision is made within the vagina.

8. The method of claim 4 wherein said incision occurs in the perineum.

9. The method of claim 4 further comprising the step of dividing the anatomical space into said inferior and superior portions.

10. The method of claim 4 wherein the step of inflating the balloon further comprising restraining an anterior portion of the balloon as a distal portion is inflated.

11. The method of claim 10 further comprising the step of releasing the anterior portion of said balloon to inflate the anterior portion of the balloon.

12. The method of claim 4 further comprising step of inverting an anterior portion of the balloon into the balloon prior to the step of introducing the balloon into the incision.

13. The method of claim 12 further comprising the step of everting and inflating the anterior portion of the balloon.

14. A method of dissecting an anatomic space adjacent a vagina, comprising the steps of:

providing a balloon mounted on a tunneling apparatus, said balloon having a distal portion and a heel portion;

making an incision to provide access to an anatomical space adjacent the vagina;

inserting said tunneling apparatus into said anatomical space, said insertion point in said anatomical space dividing said anatomical space into an inferior portion and a superior portion;

advancing said tunneling apparatus into said superior portion of said anatomical space;

pumping fluid into said balloon to inflate said distal portion of said balloon and dissect said superior portion of said anatomical space; and restraining said heal portion of said balloon against inflation.

15. The method of claim 14 further comprising the step of releasing said heel portion of said balloon to inflate said heel portion and dissect said inferior portion of said anatomical space.

16. The method of claim 14 further comprising the step of mounting a sleeve over said balloon.

17. The method of claim 16 wherein the step of pumping fluid into said balloon further comprises separating said sleeve along a weakened region.

18. The method of claim 14 further comprising the step of inverting the heel portion of the balloon into the balloon prior to inserting the tunneling apparatus into the anatomical space.

19. The method of claim 18 further comprising the step of everting and inflating the heel portion of the balloon.

* * * * *